United States Patent [19]

Weinblatt

[11] Patent Number: 4,661,847

[45] Date of Patent: Apr. 28, 1987

[54] TECHNIQUE FOR MONITORING MAGAZINE READERS

[76] Inventor: Lee S. Weinblatt, 797 Winthrop Rd., Teaneck, N.J. 07666

[21] Appl. No.: 831,234

[22] Filed: Feb. 19, 1986

[51] Int. Cl.[4] .............................................. H04N 7/14
[52] U.S. Cl. .................................... 358/108; 358/93
[58] Field of Search ................... 358/108, 93, 22, 183; 346/107 R; 128/745; 354/127.1; 434/236, 307

[56] References Cited

U.S. PATENT DOCUMENTS

| | | | |
|---|---|---|---|
| 3,158,431 | 11/1964 | Gutjahr et al. | 358/108 |
| 3,488,439 | 1/1970 | Laird et al. | 358/108 |
| 4,058,831 | 11/1977 | Smith | 358/87 |
| 4,075,657 | 2/1978 | Weinblatt | 358/93 |
| 4,326,218 | 4/1982 | Coutta et al. | 358/108 |
| 4,509,081 | 4/1985 | Peyton et al. | 358/108 |

OTHER PUBLICATIONS

Methods & Designs—Survey of Eye Movement Recording Methods, Behavior Research Methods & Instrumentation, 1975, vol. 7(5), 397–429, by Laurence R. Young and David Sheena.

*Primary Examiner*—Howard W. Britton
*Assistant Examiner*—Michael D. Parker
*Attorney, Agent, or Firm*—Thomas Langer

[57] ABSTRACT

A technique is provided for determining which pages of a selected magazine are read by a person acting as a test subject. Optic lenses are included which provide images of the magazine to a superimposing device. An image of the reader's eyes is also provided to the superimposing device so that the reader's eye movement is superimposed over the particular page being read. The superimposed optical signal is provided to a video camera which supplies it to a video monitor for real time observation as well as to a video recorder for later analysis.

11 Claims, 3 Drawing Figures

TECHNIQUE FOR MONITORING MAGAZINE READERS

BACKGROUND OF THE INVENTION

This invention is directed to a technique for monitoring individuals reading a magazine and, more particularly, to determining which pages of an open magazine are examined by the reader and which are quickly skipped over.

It is important for publishers and advertisers to know which pages in a magazine are looked at attentively by a reader. The word "magazine" is used herein to refer to any publication which when opened and placed flat on a surface presents a left page and a right page to the reader. It is well known that in the course of perusing a magazine, the attention of a reader will be attracted to certain pages and not at all to others. If an accurate and reliable method were available for determining whether the reader lingers on a given page, this information would be representative of the attraction to the reader of the contents of that particular page. Thus, for example, if an article appears on a given page, a measurement could be made by analyzing the extent to which a person's attention is drawn to that particular page. If such measurements indicate that the page does not draw the preferred degree of attention, then the caption of the article, for example, could be changed so that it becomes a stronger magnet for pulling the reader's attention to the article. Likewise, if an advertisement were to be placed on a given page, this test could be utilized to measure whether the advertisement is merely noticed and then quickly skipped over, or whether it succeeds in having the reader pay it the desired degree of attention. Such a technique is an important measurement tool for determining whether whatever is printed or displayed in the magazine functions to provide the level of exposure to the readership of the magazine that one expects by going to the expense of printing it.

The primary technique currently available to determine the level of attention devoted by a reader to a particular article or advertisement involves the interview method. A reader is selected as a test subject and asked to read a particular magazine. After the magazine is read, the person is then asked a number of questions about what was just read. However, this method is heavily dependent on recall, honesty and objectivity. It, therefore, may not accurately reflect what the reader actually experienced.

Another disadvantage of this type of technique currently in use is the unnatural, abnormal environment into which the person is placed while taking the test. The environment varies from that which the person is normally accustomed to while reading a magazine. As a result, the person may be nervous or distracted. Consequently, the test results may not be an accurate measurement of that person's reactions to the magazine under normal conditions.

Another technique for obtaining this information utilizes eye movement monitoring equipment. As described in the article "Methods & Designs, Survey of Eye Movement Recording Methods" by Laurence R. Young and David Sheena in Behavior Research Methods & Instrumentation 1975, Vol. 7(5), pages 397–427 and U.S. Pat. No. 4,075,657 issued Feb. 21, 1978, eye movement monitoring techniques bounce an infrared beam off the eye and detect the position of the reflected beam. Eye position is determined from the reflected beam position. Head position must be stabilized so that beam movement is due only to eye movement and not head movement. The eye position as indicated by the reflected beam is superimposed on an image of a magazine page. The page image can be obtained from a video camera aimed at the view displayed to the test subject.

Such equipment has several disadvantages. Firstly, equipment constraints are such that the head is pointing forward rather than downward in order to readily accommodate the infrared light source and the reflected beam detector. Therefore, a magazine would have to be placed vertically in front of the person. However, because this is not practical, slides are used to display the magazine pages. This requires extra slide equipment. Secondly, large size publications cannot be tested because of the limited angular range of eye rotation which eye movement monitoring equipment can measure (27°). Thirdly, persons wearing bifocals and contact lenses cannot be used as test subjects because such lenses disperse the infrared beam. Fourthly, due to the unnatural head rigidity and head position required which is very different from that normally used for reading, a person may not read the text for as long a time as would be the case in the "real world". Fifth, eye movement monitoring equipment is relatively heavy and bulky and is, thus, not portable. Sixth, such equipment is visible to the person and can be obtrusive and distracting. Seventh, with the equipment being visible, the person must be told that a test is being performed which, consequently, may modify the reading habits and reactions to the magazine contents. All of these factors, singly or in combination, can disturb the accuracy of the test and are, therefore, preferably to be eliminated.

SUMMARY OF THE INVENTION

It is a primary object of the present invention to provide an improved technique for determining which pages of a magazine are read by a person selected as a test subject.

Another object of the present invention is to provide an accurate and reliable technique for determining which pages in a magazine are read by a person selected as a test subject.

A further object of the present invention is to provide a relatively simple, inexpensive yet effective technique for determining which pages in a magazine are read by a person selected as a test subject.

Yet another object of the present invention is to provide an accurate and reliable technique for determining which pages in a magazine are read by a person selected as a test subject without that person being aware that his reactions are being monitored.

These and other objects of the present invention are attained by an apparatus for determining the extent to which pages in a selected publication are looked at by an individual test subject. It includes a housing and first optic means secured to the housing and placed opposite the publication for providing an image of the publications. Second optic means secured to the housing and aimed at the eyes of the individual test subject provide an image of at least one of the person's eyes, and means in the housing for superimposing the images provided by the first and second optic means.

Another aspect of the invention is directed to a method for determining the pages of a magazine read by a person selected as a test subject. It includes the steps of providing a first optic image of the left and right pages of said magazine, providing a second optic image of the eye position of the person while reading the magazine, and superimposing the first and second optic images.

BRIEF DESCRIPTION OF THE INVENTION

DETAILED DESCRIPTION OF THE PREFERRED EMBODIMENT

Figure 1:
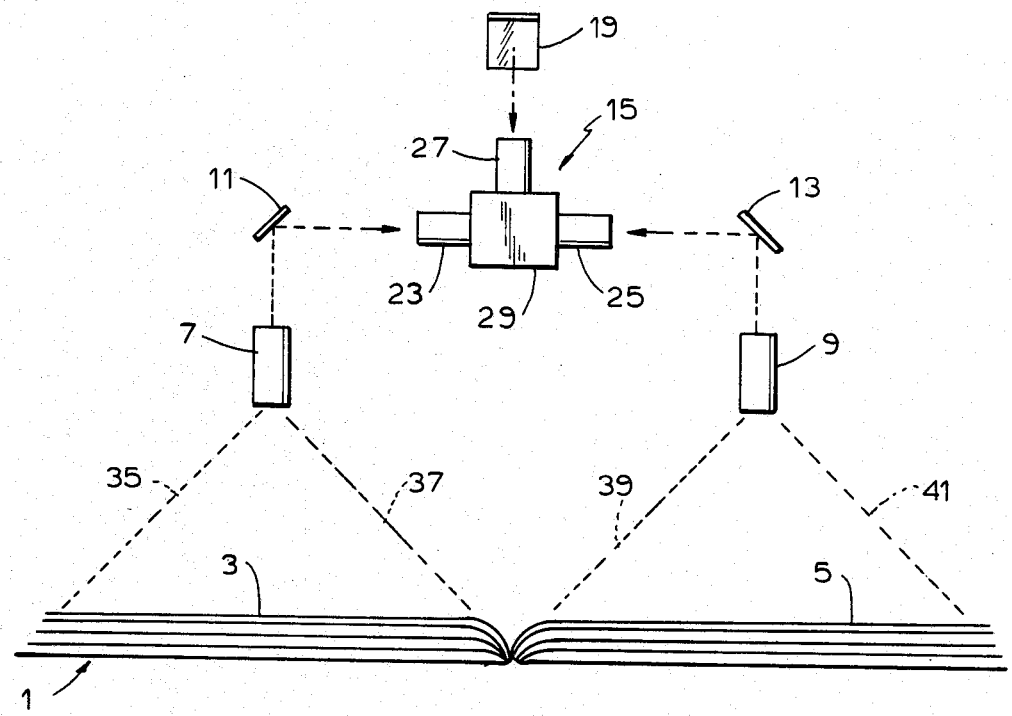
FIG. 1 is an elevational view of the relative placement of the optical elements utilized in the invention, but without the telephoto lens aimed at the eyes of the individual test subject.

The configuration of the primary optical elements of the invention is depicted in FIG. 1. A magazine 1 is shown in an open condition and lying flat on a surface (not shown) such as a table top. In this position, it normally has some of its pages on the left side and the remaining pages on the right side so that a reader can selectively look at left page 3 or right page 5. A first optic means is provided for providing an image of the magazine. It includes lens 7 which is aimed at left page 3 and lens 9 which is aimed at right page 5. These lenses are placed approximately 10 inches from the pages and must, therefore, be of a wide angle type. An 8 mm lens with a ⅔ inch camera tube provides satisfactory results.

Above each of these lenses is a fixed position mirror. Mirror 11 is associated with lens 7 while mirror 13 is associated with lens 9. The mirrors are angled relative to their respective lenses so a to direct light from the magazine through the lenses and into superimposing means 15. Light is also directed into superimposing means 15 from a telephoto lens 17 (see FIG. 2) and movable mirror 19. A 75 mm telephoto lens provides satisfactory results. Mirror 19 is mounted so as to be capable of swiveling about both a vertical and a horizontal axis. A cable and associated mounting means (not shown) similar to that used with automobile remote control mirror can be adapted for moving mirror 19.

Lens 17 is aimed at the eyes of a person who has been selected as a test subject and is placed in position in front of the magazine so as to read it, as explained in detail below. Mirror 19 is suitably angled to direct light from lens 17 into the superimposing means 15. Mirror 19 is swivellable under control of an operator in a manner described below. Suffice it to say at this point that as the eye 21 of the reader shifts with slight head movements of the person, the light from lens 17, which provides an image of eye 21, may no longer be properly directed into superimposing mean 15. Consequently, the operator who is monitoring the reading test from a hidden location swivels mirror 19 until the image of eye 21 is again properly directed into superimposing means 15. Telephoto lens 17 is also capable of some swiveling movement. It is advantageous to have this capability to provide some degree of adjustment for extreme situations as, for example, a very tall or very short person. The camera is suitably mounted and controlled by the operator to perform such movement by conventional means (not shown).

Superimposing means 15 includes lenses 23, 25 and 27. Lens 23 receives the image reflected into it by mirror 11 from lens 7. Lens 25 receives the image reflected into it by mirror 13 from lens 9. Lens 27 receives the image reflected into it from lens 17 by mirror 19. Lenses 23, 25 and 27 are coupled to an optical unit 29 which serves to superimpose all three images. Such devices are well known and can consist of mirrors, prisms, and/or lenses. One example of such a device which can be used for this purpose is manufactured by Visual Methods Incorporated of Westwood, N.J. as Model TL153.

Figure 2:
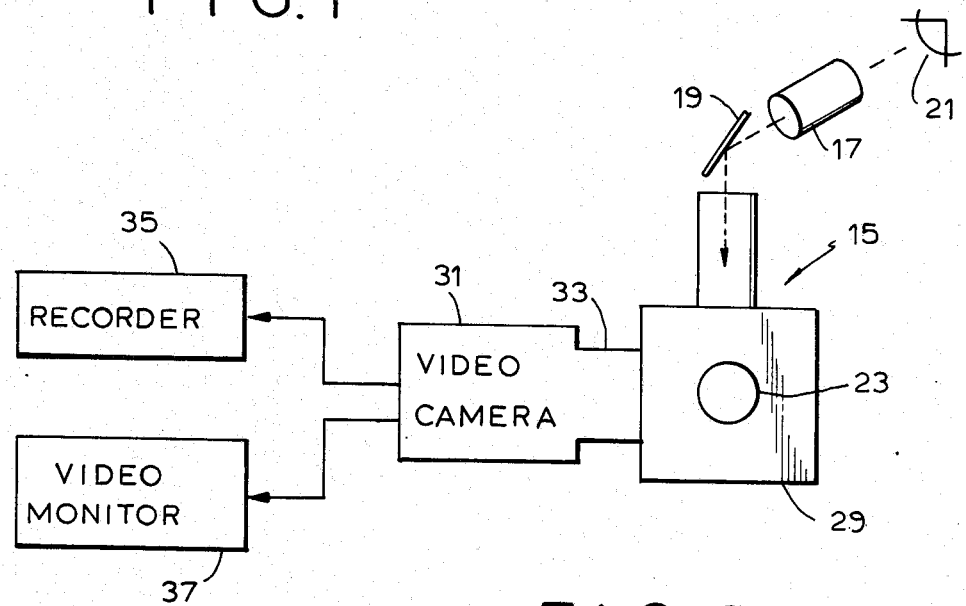
FIG. 2 is a side elevational view of the configuration shown in FIG. 1, but now showing the telephoto lens, along with a schematic circuit block diagram of the major circuit elements utilized in the invention.

As best shown in FIG. 2, a video camera 31 is also optically coupled to optical unit 29. The superimposed image of the magazine and the reader's eyes are directed into the lens 33 of video camera 31. Video signals from video camera 31 are provided to a video recorder 35 as well as to a video monitor 37. The results of the test are stored on recorder 35 for later analysis by experts who interpret its results. A video monitor 37 is used during the course of the test by a system operator who constantly watches what is occurring. Therefore, should the reader's head be moved somewhat during the test, the eyes may no longer be displayed at all on the video monitor or may no longer be accurately superimposed on the magazine so that it would be impossible to determine which page is being read. When this occurs, the operator swivels mirror 19 with the remote control cable (not shown) until the proper superimposition is regained.

All of the above-described components of the system are well known. Lenses 7 and 9 are, as stated above, wide angle lenses suitably selected for the distance between them and magazine 1 as well as for the field of view defined by broken lines 35 and 37 for the left page 3 and lines 39 and 41 for the right hand page. Likewise, mirrors 11, 13 and 19 are conventional. Lenses 23, 25 and 27 merely convey light into optical unit 29. Optical unit 29 itself has been described above as a particular model now available from Visual Methods Incorporated. Telephoto lens 1 is also conventionally available with its characteristics selected for the particular distance between it and the reader's eyes. Accordingly, it is not believed that further details of any of these components are required and, in order not to unnecessarily complicate this disclosure, none are provided outside of the details discussed above.

Figure 3:
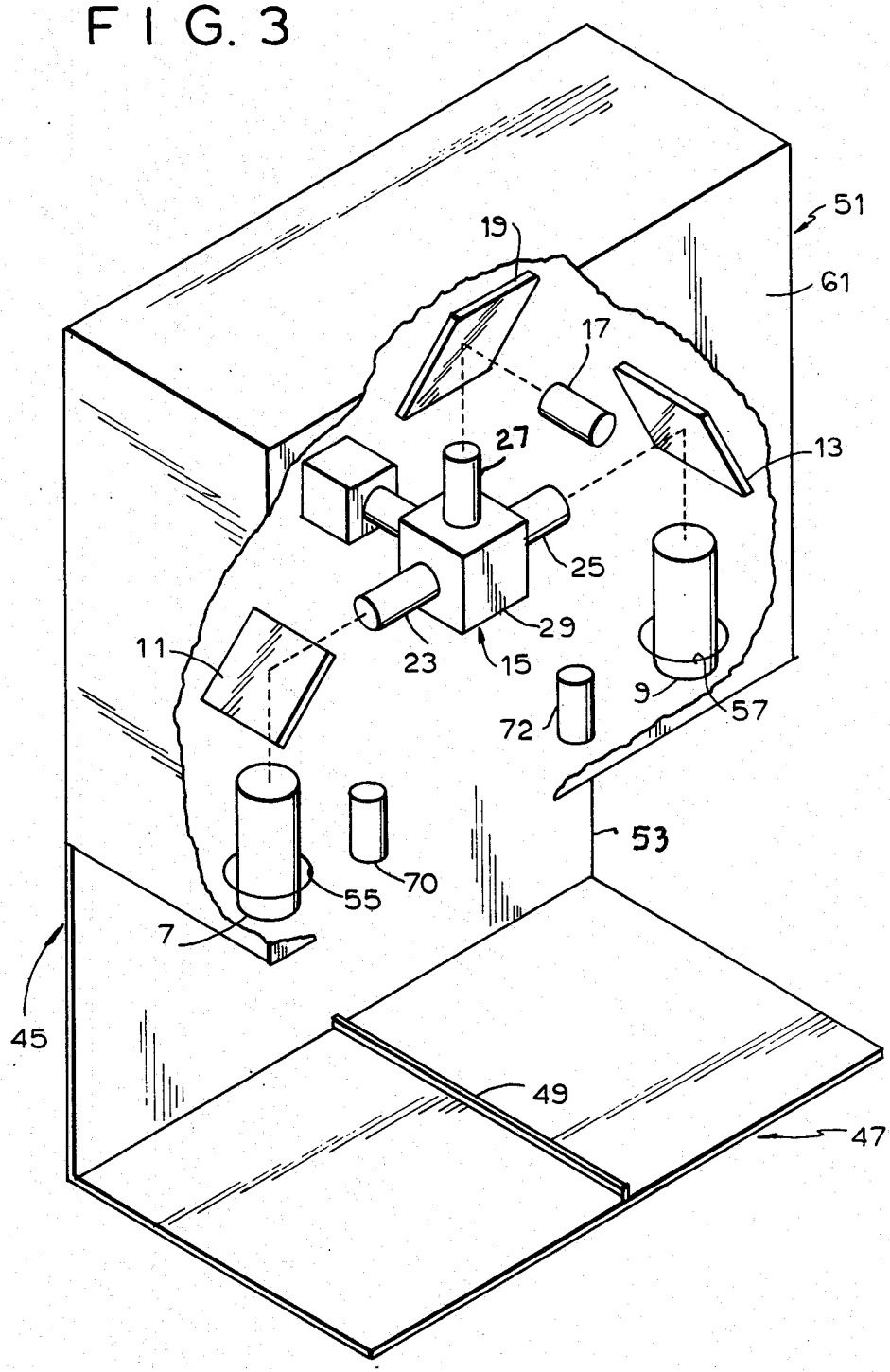
FIG. 3 is a perspective view showing the invention and including the support housing the optical and circuit elements, but with certain portions cut away for clarity of presentation.

The actual unit which houses all of these components is drawn in a perspective view depicted by FIG. 3. Housing 45 includes a support 47 which lies on a flat surface (not shown), such as a tabletop, on which magazine 1 also rests. Base 47 includes a metal rod 49 under which the spine of magazine 1 is positioned. In this manner rod 49 holds magazine 1 in place relative to the optical equipment utilized in this apparatus. Overhang 51 is spaced vertically from base 47 and kept in position by back wall 53. Overhang 51 extends forward somewhat toward the reader and lies above magazine 1 when it is placed into base 47. Lens 7 is secured to housing 45 and is directed at left hand page 3 through opening 55. Mirror 11 is positioned above lens 7 and is secured to housing 45. Likewise, lens 9 is secured to housing 45 and is positioned within opening 57. Mirror 13 is secured to housing 45 above lens 9. Superimposing means 15 is secured to housing 45 and includes optical unit 29 to which lenses 23, 25 and 27 are secured. Telephoto lens 17 is also secured to housing 45 and is aimed at the reader's eyes through an opening (not shown) in front wall 61 of overhang 51. Mirror 19 is secured to housing 5 so as to direct light from lens 17 into lens 27.

In addition to all of the above-described components, housing 45 also carries two lamps 70 and 72. As shown in FIG. 3, these lamps are attached to overhang 51. Lamp 70 shines light on left page 3 while lamp 72 shines light on right page 5. The lamps are connected to a power supply via a switch (not shown). The purpose of these lamps, other than the obvious one of providing illumination, is discussed below.

In operation, magazine 1 is placed into base 47 of housing 45 so that when it is open exactly in half, rod 49 secures its spine to the housing. The pages of the magazine can then be freely turned. It will always present a left page 3 and a right page 5 to the reader. A reader is selected and asked to read magazine 1. The person is requested to remain in front of housing 45 while reading. Overhang 51 of housing 45 is sized so as not to interfere with the line of sight from the reader's eyes to any portion of the pages of the magazine.

In order to keep the person relaxed and at ease, it is preferable not to divulge that a test is being conducted. The person can simply be asked to read a maga ine for amusement. Alternatively, the person can be told that certain questions may later be asked about the magazine, but that no time limit is set for completing the reading. Any such approaches can be utilized in order to keep from applying pressure and tension to the reader. In this regard, lamp 70 and 72 come into play. Naturally, when the reader is placed before housing 45 one has the tendency to be curious or suspicious. To cut off these feelings, the operator flicks on a switch and lamps 70 and 72 are illuminated. The test subject then assumes that housing 45 merely supports lamps 70 and 72 along with magazine for the reader's convenience. Thus, a relaxed state of mind and, therefore, more accurate and realistic reactions are obtained.

Initially, the equipment is calibrated to each individual test subject. Each person is encouraged to look at the cover page of the closed magazine. With the magazine closed, the cover page corresponds to the right page 5 in FIG. 1. This can be readily accomplished by simply placing a set of suggestions on the cover page. These can say practically anything, just as long as they are effective to keep the person's eyes on them long enough for the operator to complete the calibration. This is merely a matter of a few seconds. Mirror 19 is adjusted by the operator (who is out of sight) so that accurate superimposition of the person's eyes over the right page is obtained. It is also at this time that the direction of telephoto lens 17 is changed to accommodate unusual conditions, as discussed above.

As the reader flips the pages of the magazine, lens 7 is constantly aimed at the left page while lens 9 is constantly aimed at the right page. The images of these pages is input to superimposing means 15. Telephoto lens 17 is aimed at the reader's eyes. This image is input to superimposing means 15 via mirror 19. The superimposing means 15 feeds an optical signal to video camera 31 which, in turn, inputs a video signal to recorder 35 of video monitor 37. An operator watching video monitor 37 determines whether everything during the test is normal. Should the reader move so that his eyes are no longer displayed as superimposed on the magazine, the operator swivels mirror 19 to regain the proper image superimposition. As the images from the magazine pages and the reader's eyes are superimposed, it is very easy to tell whether the reader is looking at the left page or the right page. In addition, the images stored on recorder 35 reveal the length of time the reader lingered on a particular page, whether he returned to it, and also those pages which were summarily skipped as holding no interest whatsoever for the reader. Each page can be separately analyzed because it is shown individually. Thus, no complex techniques are required to backtrack which page involved what reader reactions. Everything is readily available on each superimposed image to provide the tools for rendering a complete analysis of the test results. Based on the test results, it is relatively simple to determine whether a particular page was of absolutely no interest to the reader, or the degree of interest it held for the reader based on the amount of time it held the reader's attention.

All the disadvantages of eye movement monitoring are avoided with this invention. Head position need not be kept rigid because mirror 19 is moved by the monitoring operator to keep the image from lens 17 in proper position. A separate slide projector is not required. Large size publications can be used because the entire range of eye motion can be monitored by lens 17 rather than being restricted to only that range of eye motion which can be picked up by a reflected beam. Bifocals and contact lenses are not a problem because eye motion is picked up by lens 17 even if the person is wearing them. A normal reading position of looking down at the pages is assumed. This coupled with the ability to move the head allows the person to maintain a normal reading habit and attention span. Housing 45 is relatively light and small and can, therefore, be readily moved from site to site if necessary to obtain willing test subjects. Finally, the equipment of the invention is camouflaged to keep the person from being distracted by a test environment.

Although a preferred embodiment of the present invention has been described above, it should be apparent that various modifications can readily be made to it. For example, lenses 23, 25 and 27 which are shown as separate devices coupled to optical unit 29 are not necessarily required. A particular optical unit 29 can dispense with these lenses. For example, an optical pipe can be used which includes relay lenses inside a tube. Also, fiber optics can be utilized. In addition, although a particular type of optical unit 29 and superimposing means 15 have been disclosed, various other types can be utilized. These and other such modifications are intended to be included within the scope of the invention as defined by the following claims.

I claim:

1. Apparatus for determining the extent to which pages in a selected publication are looked at by an individual test subject, comprising:
    a housing;
    first optic means secured to said housing and placed opposite the publication for providing an image of said publication;
    second optic means secured to said housing and aimed at the eyes of the individual test subject to provide an image of at least one of said eyes; and
    means in said housing for superimposing the images provided by the said first and second optic means.

2. The apparatus of claim 1, wherein a selected publication, when laid in an open position, has a left page and a right page, and wherein said first optic means comprises one lens adapted to provide an image of the left page of said publication and another lens adapted to provide an image of the right page of said publication.

3. The apparatus of claim 2, wherein said lenses are wide angle lenses.

4. The apparatus of claim 3, wherein said first optic means is secured to a portion of said housing overhanging said publication.

5. The apparatus of claim 1, wherein said second optic means comprises a telephoto lens.

6. The apparatus of claim 1, wherein said superimposing means comprises an optical unit and mirror means for directing the images from said first and second optical means to said optical unit.

7. The apparatus of claim 6, wherein the mirror means includes a first mirror swivelably mounted in said housing and receiving the image from said second optic means.

8. The apparatus of claim 7, wherein said first mirror is connected to position control means for selectively setting the swivelable position of said first mirror.

9. The apparatus of claim 8, further comprising video means for detecting the superimposed images produced by said superimposing means.

10. The apparatus of claim 9, further comprising means coupled to said video means for displaying the superimposed images.

11. The apparatus of claim 9, further comprising means for recording the output of said video means.

* * * * *